(12) United States Patent
Biggadike et al.

(10) Patent No.: US 7,405,206 B2
(45) Date of Patent: Jul. 29, 2008

(54) ANTI-INFLAMMATORY ANDROSTANE DERIVATIVES

(75) Inventors: Keith Biggadike, Stevenage (GB); Paul Jones, Stevenage (GB); Jeremy John Payne, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 489 days.

(21) Appl. No.: 10/492,813

(22) PCT Filed: Oct. 17, 2002

(86) PCT No.: PCT/EP02/11634

§ 371 (c)(1), (2), (4) Date: Sep. 20, 2004

(87) PCT Pub. No.: WO03/035668

PCT Pub. Date: May 1, 2003

(65) Prior Publication Data

US 2005/0054622 A1 Mar. 10, 2005

(30) Foreign Application Priority Data

Oct. 20, 2001 (GB) ................................ 0125259.2

(51) Int. Cl.
- *A61K 31/58* (2006.01)
- *A61K 31/585* (2006.01)
- *C07J 17/00* (2006.01)

(52) U.S. Cl. .......................... 514/172; 514/175; 540/2; 540/114; 540/115

(58) Field of Classification Search ...................... 540/2, 540/114, 115; 552/610; 514/172, 175
See application file for complete search history.

(56) References Cited

U.S. PATENT DOCUMENTS

| | | | |
|---|---|---|---|
| 3,828,080 A | 8/1974 | May et al. | |
| 3,856,828 A | 12/1974 | Phillipps et al. | |
| 6,537,983 B1 * | 3/2003 | Biggadike et al. | 514/172 |
| 6,750,210 B2 * | 6/2004 | Biggadike | 514/172 |
| 6,759,398 B2 * | 7/2004 | Biggadike | 514/172 |
| 6,777,399 B2 * | 8/2004 | Biggadike et al. | 514/172 |
| 6,777,400 B2 * | 8/2004 | Biggadike et al. | 514/172 |
| 6,787,532 B2 * | 9/2004 | Biggadike et al. | 514/172 |
| 6,858,593 B2 * | 2/2005 | Biggadike et al. | 514/100 |
| 6,858,596 B2 * | 2/2005 | Biggadike et al. | 514/172 |
| 6,878,698 B2 * | 4/2005 | Biggadike et al. | 514/172 |
| 7,101,866 B2 * | 9/2006 | Biggadike et al. | 514/172 |
| 7,125,985 B2 * | 10/2006 | Biggadike et al. | 540/114 |
| 2004/0028615 A1 * | 2/2004 | Briggadike et al. | 424/45 |
| 2004/0220156 A1 * | 11/2004 | Biggadike et al. | 514/172 |
| 2004/0224932 A1 * | 11/2004 | Biggadike et al. | 514/172 |
| 2005/0020549 A1 * | 1/2005 | Biggadike et al. | 514/172 |
| 2005/0043284 A1 * | 2/2005 | Biggadike et al. | 514/172 |
| 2005/0130947 A1 * | 6/2005 | Biggadike | 514/172 |
| 2005/0152845 A1 * | 7/2005 | Biggadike et al. | 424/46 |
| 2005/0164996 A1 * | 7/2005 | Biggadike et al. | 514/172 |
| 2005/0164997 A1 * | 7/2005 | Biggadike | 514/172 |
| 2005/0175545 A1 * | 8/2005 | Biggadike et al. | 424/46 |
| 2006/0247219 A1 * | 11/2006 | Biggadike et al. | 514/176 |
| 2007/0027128 A1 * | 2/2007 | Biggadike et al | 514/172 |

FOREIGN PATENT DOCUMENTS

| | | |
|---|---|---|
| EP | 0057401 | 8/1982 |
| WO | 9724365 A | 7/1997 |
| WO | WO 97/24365 | 7/1997 |

OTHER PUBLICATIONS

Isogai et al., "Binding affinities of mometasone furoate and related compounds including its metabolites for the glucocorticoid receptor of rat skin tissue," *Journal of Steroid Biochemistry and Molecular Biology* 44(2):141-145 (1993).

Popper et al., "Structure-activity relationship of a series of novel topical corticosteroids," *Journal of Steroid Biochemistry* 27(4-6):837-843 (1987).

Shapiro et al., "17 Heteroaroyl esters of corticosteroids 2. 11-beta hydroxyl series," *Journal of Medicinal Chemistry* 30(9): 1581-1588 (1987).

(Continued)

*Primary Examiner*—Barbara P Badio
(74) *Attorney, Agent, or Firm*—James P. Riek

(57) ABSTRACT

There are provided compounds of formula (I)

wherein
$R_1$ represents O, S or NH;
$R_2$ represents —C(=O)-aryl or —C(=O)-heteroaryl;
$R_3$ represents hydrogen, methyl (which may be in either the α or β configuration) or methylene;
$R_4$ and $R_5$ are the same or different and each represents hydrogen or halogen; and
═══represents a single or a double bond;
and salts and solvates thereof;
process for preparing them, compositions containing them and their use in therapy.

26 Claims, No Drawings

OTHER PUBLICATIONS

Isogai M. et al; "Binding Affinities of Mometasone Furoate and Related Compounds Including its Metabolites for the Glucocorticoid Receptor of Rat Skin Tissue"; Journal of Steroid Biochemistry and Molecular Biology; 1993; 44, 2; 141-145; Elsevier Science Ltd.; Oxford, GB.

Popper T.L. et al; "Structure-Activity Relationship of a Series of Novel Topical Corticosteroids"; Journal of Steroid Biochemistry; 1987; 27, 4-6; 837-843; Pergamon Press PLC; GB.

Shapiro E.L. et al; "17 Heteroaroyl Esters of Corticosteroids 2. 11-Beta Hydroxy Series"; Journal of Medicinal Chemistry; 1987; 30, 9; 1581-1588; American Chemical Society; Washington, US.

* cited by examiner

ANTI-INFLAMMATORY ANDROSTANE DERIVATIVES

CROSS-REFERENCE TO RELATED APPLICATIONS

This application is filed pursuant to 35 USC 371 as a U.S. National Phase Application of International Patent Application Ser. No. PCT/EP02/11634 filed on 17 Oct. 2002, which claims priority from GB 0125259.2 filed on 20 Oct. 2001 in the United Kingdom.

FIELD OF THE INVENTION

The present invention relates to novel anti-inflammatory and anti-allergic compounds of the androstane series and to processes for their preparation. The present invention also relates to pharmaceutical formulations containing the compounds and to therapeutic uses thereof, particularly for the treatment of inflammatory and allergic conditions.

BACKGROUND OF THE INVENTION

Glucocorticosteroids which have anti-inflammatory properties are known and are widely used for the treatment of inflammatory disorders or diseases such as asthma and rhinitis. However, glucocorticosteroids in general may suffer from the disadvantage of causing unwanted systemic effects following administration. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced it remains an object of research to produce new molecules which have excellent anti-inflammatory properties, with predictable pharmacokinetic and pharmacodynamic properties, with an attractive side effect profile, and with a convenient treatment regime.

WO94/13690, WO94/14834, WO92/13873, WO92/13872, WO 97/24365, WO 97/24367 and WO 97/24368 all disclose glucocorticosteroids which are alleged to possess anti-inflammatory activity coupled with reduced systemic potency. Certain novel androstane derivatives are disclosed in WO02/12265, WO02/12266 (Glaxo Group) and WO02/00679 (Novartis), these three documents being published after the earliest priority date of this patent application.

SUMMARY OF THE INVENTION

The present invention provides a novel group of compounds which possess useful and long lasting anti-inflammatory activity whilst having little or no systemic activity. Thus, the compounds of the present invention represent a safer alternative to those known glucocorticoids which have poor side-effect profiles.

Thus, according to one aspect of the invention, there is provided a compound of formula (I)

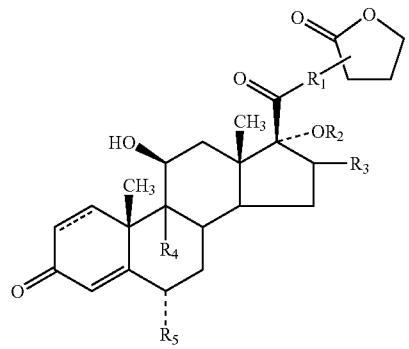

wherein
$R_1$ represents O, S or NH;
$R_2$ represents —C(=O)-aryl or —C(=O)-heteroaryl;
$R_3$ represents hydrogen, methyl (which may be in either the α or β configuration) or methylene;
$R_4$ and $R_5$ are the same or different and each represents hydrogen or halogen; and
=====represents a single or a double bond;
and salts and solvates thereof.

References to the term "aryl" include references to phenyl which may be optionally substituted with one or more substituents.

References to the term "heteroaryl" include references to 5 or 6 membered heterocyclic aromatic rings containing 1-3 hetero atoms selected from N, O and S (e.g. thiophenyl (eg thiophen-2-yl or thiophen-3-yl), furanyl (eg furan-2-yl or furan-3-y), pyrrolyl (eg 1H-pyrrol-2-yl), thiadiazolyl (eg 1,2,3-thiadiazol-5-yl, or 1,2,3-thiadiazol-4-yl)). Further examples include thiazolyl (eg 1,3-thiazolyl-5-yl or 1,3-thiazolyl-4-yl), isoxazolyl (eg isoxazol-5-yl, isoxazol-4-yl or isoxazol-3-yl), isothiazolyl (eg isothiazol-3-yl or isothiazol-5-yl) and pyrazolyl (eg 1H-pyrazol-5-yl).

All of the previously named heterocycles may be optionally substituted with one or more (e.g. 1 or 2) substituents.

Examples of substituents for aryl and heteroaryl include $C_{1-6}$alkyl (e.g. methyl), halogen (e.g. chlorine or bromine) or $C_{1-6}$ alkoxy (e.g. methoxy or ethoxy).

Examples of substituted furanyl include 3-Me-furan-2-yl, 5-Br-furan-2-yl, 2-Me-furan-3-yl and 2,5-diMe-furan-3-yl. Examples of substituted thiophenyl include 5-Me-thiophen-2-yl, 5-Cl-thiophen-2-yl, 3-Cl-thiophen-2-yl, 3-Br-thiophen-2-yl, 4-methoxy-thiophen-3-yl, 2,5-diCl-thiophen-3-yl and 4-methoxy-5-Cl-thiophen-3-yl. Examples of substituted pyrrolyl include 1-Me-1H-pyrrol-2-yl. Examples of substituted thiadiazolyl include 4-Me-1,2,3-thiadiazol-5-yl. Examples of substituted isoxazolyl include 3-Me-isoxazol-5-yl, 5-Me-isoxazol-3-yl and 3,5-diMe-isoxazol-4-yl. Examples of substituted pyrazolyl include 1,3-diMe-1H-pyrazol-5-yl.

Examples of solvates include hydrates.

Examples of salts of compounds of formula (I) include physiologically acceptable salts which may be formed with basic compounds (such as when heteroaryl is basic) eg. acetate, benzoate, citrate, succinate, lactate, tartrate, fumarate and maleate.

References hereinafter to a compound according to the invention includes both compounds of formula (I) and salts and solvates thereof, particularly pharmaceutically acceptable salts and solvates.

It will be appreciated that the invention includes within its scope all stereoisomers of the compounds of formula (I) and mixtures thereof.

Preferably, the absolute stereochemistry will be as shown in the representation of compounds of formula (I).

In particular the compounds of formula (I) contain an asymmetric centre at the point of attachment of the lactone moiety. Thus, the invention includes within its scope both diastereoisomers at this asymmetric centre and mixtures thereof.

We prefer $R_1$ to represent O or S, especially S.

$R_1$ can be bonded to the alpha, beta or gamma carbon atoms of the lactone group,

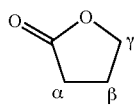

We prefer that $R_1$ is bonded to the alpha atom of the lactone group.

We prefer $R_2$ to represent —C(=O)-heteroaryl. Preferably the heteroaryl is a 5-membered heterocyclic aromatic ring containing 1 to 3 heteroatoms selected from O, N and S which may optionally be substituted. In one respect, preferably heteroaryl represents furanyl, pyrrolyl or thiophenyl, more preferably furanyl or thiophenyl eg 2-furanyl, 3-furanyl, 2-thiophenyl or 3-thiophenyl, especially furanyl, particularly 2-furanyl.

Of particular interest are compounds in which the heteroaryl is a 5-membered heterocyclic aromatic ring containing 2 heteroatoms selected from O, N and S. Thus a further set of preferred compounds is that in which $R_2$ represents optionally substituted thiazolyl. A further set of preferred compounds is that in which $R_2$ represents optionally substituted isothiazolyl. A further set of preferred compounds is that in which $R_2$ represents optionally substituted pyrazolyl. A further set of preferred compounds is that in which $R_2$ represents optionally substituted isoxazolyl.

Of particular interest is compounds in which the heteroaryl is a 5-membered heterocyclic aromatic ring containing 3 heteroatoms selected from O, N and S. Thus a further set of preferred compounds is that in which $R_2$ represents optionally substituted thiadiazolyl.

Compounds in which $R_2$ represents —C(=O)-aryl (preferably aryl represents phenyl) are also of particular interest.

We prefer $R_3$ to represent methyl, especially methyl in the α configuration. Compounds in which $R_3$ represents methyl in the β configuration are also of particular interest.

Compounds of formula (I) in which $R_4$ and $R_5$, which can be the same or different, each represents hydrogen, fluorine or chlorine, particularly hydrogen or fluorine, are preferred. Especially preferred are compounds in which both $R_4$ and $R_5$ are fluorine.

Preferably, ----represents a double bond. Compounds in which ----represents a single bond are also of particular interest.

A particularly preferred group of compounds of the present invention are compounds of formula (I) in which $R_1$ is S; $R_2$ is —C(=O)-2-furanyl; $R_3$ is methyl; $R_4$ and $R_5$, which can be the same or different, each represents hydrogen or fluorine, especially fluorine, and ----represents a single or a double bond.

It is to be understood that the present invention covers all combinations of particularly and preferred groups referred to hereinabove.

Preferred compounds of formula (I) include: 6α, 9α-difluoro-17α-[(2-furanylcarbonyl)oxy]-11β-hydroxy-16α-methyl-3-oxo-androsta-1,4-diene-17β-carbothioic acid S-(2-oxo-tetrahydro-furan-3-yl)ester or a solvate thereof, particularly 6α,9α-difluoro-17α-[(2-furanylcarbonyl)oxy]-11β-hydroxy-16α-methyl-3-oxo-androsta-1,4-diene-17β-carbothioic acid S-(2-oxo-tetrahydro-furan-3S-yl)ester or a solvate thereof.

It will be appreciated that each of the above compounds of formula (I) includes the individual R and S diastereoisomers at the asymmetric centre at the point of attachment of the lactone moiety as well as the mixtures thereof. Thus, the individual R and S diastereoisomers isolated such as to be substantially free of the other diastereoisomer i.e. pure and mixtures thereof are included within the scope of the present invention. An individual R or S diastereoisomer isolated such as to be substantially free of the other diastereoisomer i.e. pure will preferably be isolated such that less than 10% preferably less than 1% especially less than 0.1% of the other diastereoisomer is present.

The compounds of formula (I) have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) are useful in the treatment of inflammatory and/or allergic disorders. Further, compounds of formula (I) possess the advantage of having little or no systemic activity. Therefore, the compounds of the invention may represent a safer alternative to those known anti-inflammatory glucocorticoids which have poor side effect profiles.

Examples of disease states in which the compounds of the invention have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) are useful in human or veterinary medicine, in particular as anti-inflammatory and anti-allergic agents.

There is thus provided as a further aspect of the invention a compound of formula (I) or a physiologically acceptable salt or solvate thereof for use in human or veterinary medicine, particularly in the treatment of patients with inflammatory and/or allergic conditions.

According to another aspect of the invention, there is provided the use of a compound of formula (I) or physiologically acceptable salt or solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable salt or solvate thereof. There is also provided the use of a compound of formula (I) or physiologically acceptable salt or solvate thereof for the treatment of patients with inflammatory and/or allergic conditions.

The compounds according to the invention may be formulated for administration in any convenient way, and the invention therefore also includes within its scope pharmaceutical compositions comprising a compound of formula (I) or physiologically acceptable salt or solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Advantageously compositions for topical administration to the lung include dry powder compositions and spray compositions.

Dry powder compositions for topical delivery to the lung may, for example, be presented in capsules and cartridges for use in an inhaler or insufflator of, for example, gelatine. Formulations generally contain a powder mix for inhalation of the compound of the invention and a suitable powder base such as lactose or starch. Each capsule or cartridge may generally contain between 20 μg-10 mg of the compound of formula (I). Alternatively, the compound of the invention may be presented without excipients. Packaging of the formulation may be suitable for unit dose or multi-dose delivery. In the case of multi-dose delivery, the formulation can be pre-metered (eg. as in Diskus, see GB 2242134 or Diskhaler, see GB 2178965, 2129691 and 2169265) or metered in use (eg. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol. One example formulation is excipient free and consists essentially of (eg consists of) a compound of formula (I) (optionally together with another active ingredient) and a propellant selected from 1,1,1,2-tetrafluoroethane, 1,1,1,2,3,3,3-heptafluoro-n-propane and mixture thereof. Another example formulation comprises particulate compound of formula (I), a propellant selected from 1,1,1,2-tetrafluoroethane, 1,1,1,2,3,3,3-heptafluoro-n-propane and mixture thereof and a suspending agent which is soluble in the propellant eg an oligolactic acid or derivative thereof as described in WO94/21229. The preferred propellant is 1,1,1,2-tetrafluoroethane. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of compound of formula (I) as produced may be size reduced by conventional means eg. by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (eg as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04327). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Formulations for administration topically to the nose include pressurised aerosol formulations and aqueous formulations administered to the nose by pressurised pump.

Aqueous formulations for administration to the lung or nose may be provided with conventional excipients such as buffering agents, tonicity modifying agents and the like. Aqueous formulations may also be administered to the nose by nebulisation.

Other possible presentations include the following: Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

If appropriate, the formulations of the invention may be buffered by the addition of suitable buffering agents.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will usually be within the range of from 0.1 to 5%.

Aerosol formulations are preferably arranged so that each metered dose or "puff" of aerosol contains 1 µg-2000 µg eg 20 µg-2000 µg, preferably about 20 µg-500 µg of a compound of formula (I). Administration may be once daily or several times daily, for example 2, 3, 4 or 8 times, giving for example 1, 2 or 3 doses each time. Preferably the compound of formula (I) is delivered once or twice daily. The overall daily dose with an aerosol will typically be within the range 10 µg-10 mg eg 100 µg-10 mg preferably, 200 µg-2000 µg.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $P_2$ adrenoreceptor agonist, an anti-histamine or an anti-allergic. The invention thus provides, in a further aspect, a combination comprising a compound of formula (I) or a physiologically acceptable salt or solvate thereof together with another therapeutically active agent, for example, a $\beta_2$-adrenoreceptor agonist, an anti-histamine or an anti-allergic.

Combinations with long acting $\beta_2$ adrenoreceptor agonists are preferred, especially those capable of providing a therapeutic effect over 24 hours. There is, for example, provided a pharmaceutical composition suitable for once-per-day administration comprising a compound of formula (I) or a salt or solvate thereof in combination with a long acting $\beta_2$ adrenoreceptor agonist.

Examples of $\beta_2$-adrenoreceptor agonists include salmeterol (eg as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long acting $\beta_2$-adrenoreceptor agonists, such as salmeterol or fomoterol, are preferred.

Preferred long acting $\beta_2$-adrenoreceptor agonists include those described in WO 266422A.

Especially preferred long-acting $\beta_2$-adrenoreceptor agonists are compounds of formula (X)

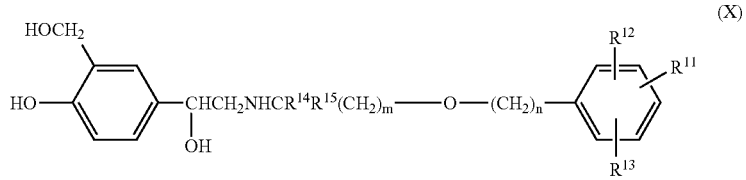

or a salt or solvate thereof, wherein:

m is an integer of from 2 to 8;

n is an integer of from 3 to 11, preferably from 3 to 7;

with the proviso that m+n is 5 to 19, preferably 5 to 12;

$R^{11}$ is —$XSO_2NR^{16}R^{17}$ wherein X is —$(CH_2)_p$— or $C_{2-6}$alkenylene;

$R^{16}$ and $R^{17}$ are independently selected from hydrogen, $C_{1-6}$alkyl, $C_{3-7}$cycloalkyl, $C(O)NR^{18}R^{19}$, phenyl, and phenyl ($C_{1-4}$alkyl)-, or $R^{16}$ and $R^{17}$, together with the nitrogen to which they are bonded, form a 5-, 6-, or 7-membered nitrogen containing ring, and $R^{16}$ and $R^{17}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{18}$, —$SO_2NR^{18}R^{19}$, —$CONR^{18}R^{19}$, —$NR^{18}C(O)R^{19}$, or a 5-, 6- or 7-membered heterocyclic ring;

$R^{18}$ and $R^{19}$ are independently selected from hydrogen, $C_{1-6}$alkyl, $C_{3-6}$cycloalkyl, phenyl, and phenyl ($C_{1-4}$alkyl)—; and p is an integer of from 0 to 6, preferably from 0 to 4;

$R^{12}$ and $R^{13}$ are independently selected from hydrogen, $C_{1-6}$alkyl, $C_{1-6}$alkoxy, halo, phenyl, and $C_{1-6}$haloalkyl; and $R^{14}$ and $R^{15}$ are independently selected from hydrogen and $C_{1-4}$alkyl with the proviso that the total number of carbon atoms in $R^{14}$ and $R^{15}$ is not more than 4.

In the compounds of formula (I) the group $R^{11}$ is preferably attached to the meta-position relative to the —O—$(CH_2)_n$— link.

$R^{11}$ preferably represents —$SO_2NR^{16}R^{17}$ wherein $R^{16}$ and $R^{17}$ are independently selected from hydrogen and $C_{1-6}$alkyl, more preferably $R^{11}$ is —$SO_2NH_2$.

$R^{14}$ and $R^{15}$ are preferably independently selected from hydrogen and methyl, more preferably $R^{14}$ and $R^{15}$ are both hydrogen.

m is suitably 4, 5, or 6, and n is suitably 3, 4, 5 or 6. Preferably m is 5 or 6 and n is 3 or 4, such that m+n is 8, 9 or 10, preferably 9.

More especially preferred compounds of formula (X) are compounds of formula (Xa)

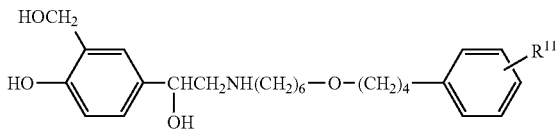

(Xa)

or a salt or solvate thereof, wherein
$R^{11}$ is as defined above for formula (X).

Further more especially preferred compounds of formula (X) are compounds of formula (Xb):

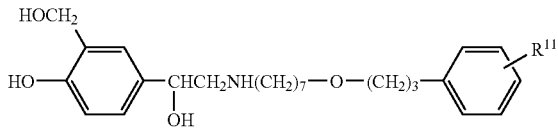

(Xb)

or a salt or solvate thereof, wherein
$R^{11}$ is as defined above for formula (X).

In the compounds of formulae (Xa) and (Xb), the group $R^{11}$ is preferably attached to the meta-position relative to the —O—$(CH_2)_4$— or —O—$(CH_2)_3$— link respectively.

In the compounds of formulae (Xa) and (Xb), $R^{11}$ is preferably —$SO_2NR^{16}R^{17}$ wherein $R^{16}$ and $R^{17}$ are independently selected from hydrogen and $C_{1-6}$alkyl, more preferably $R^{11}$ is —$SO_2NH_2$.

In the definition of $R^{11}$ where '$R^{16}$ and $R^{17}$ together with the nitrogen atom to which they are bonded, form a 5-, 6-, or 7-membered nitrogen containing ring', the term "5-, 6-, or 7-membered nitrogen containing ring" means a 5-, 6-, or 7-membered saturated or unsaturated ring which includes the sulfonamide nitrogen atom and optionally 1 or 2 other heteroatoms independently selected from nitrogen, sulphur, and oxygen. Suitable examples of such a ring include piperidinyl, morpholinyl, and piperazinyl.

In the definition of $R^{11}$, specifically the optional substituents on $R^{16}$ and $R^{17}$, the term "5-, 6-, or 7-membered heterocyclic ring" means a 5-, 6-, or 7-membered fully or partially saturated or unsaturated ring which includes 1, 2, 3 or 4 heteroatoms independently selected from nitrogen, sulphur, and oxygen. Suitable examples of such a ring include pyrrolyl, furyl, thienyl, pyridinyl, pyrazinyl, pyridazinyl, imidazolyl, tetrazolyl, tetrahydrofuranyl, oxazolyl, thiazolyl, thiadiazolyl, piperidinyl, morpholinyl, and piperazinyl.

In the definition of X, the term "alkenylene" includes both cis and trans structures. Suitable examples of alkenylene groups include —CH═CH—.

The compounds of formulae (X), (Xa) and (Xb) include an asymmetric centre, namely the carbon atom of the

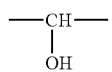

group. The present invention includes both (S) and (R) enantiomers either in substantially pure form or admixed in any proportions.

Similarly, where $R^{14}$ and $R^{15}$ are different groups, the carbon atom to which they are attached is an asymmetric centre and the present invention includes both (S) and (R) enantiomers at this centre either in substantially pure form or admixed in any proportions.

Thus the compounds of formulae (X), (Xa) and (Xb) include all enantiomers and diastereoisomers as well as mixtures thereof in any proportions.

The most preferred compound of formula (X) is 3-(4-{[6-({(2R)-2-Hydroxy-2-[4-hydroxy-3-(hydroxymethyl)phenyl]ethyl}amino)-hexyl]oxy}butyl)benzenesulfonamide or a salt or solvate thereof.

Salts and solvates of compounds of formulae (X), (Xa) and (Xb) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formulae (X), (Xa) and (Xb) and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Compounds of formula (X), (Xa) and (Xb) may be prepared by reference to Example X recited below, by analogous processes, or by other conventional processes known per se.

Since the compounds of formula (I) are expected to be long-acting, preferably the composition comprising the compound of formula (I) and the long-acting $\beta_2$-adrenoreceptor agonists will be delivered once-per-day and the dose of each will be selected so that the composition has a therapeutic effect in the treatment of respiratory disorders effect (eg in the treatment of asthma or COPD, particularly asthma) over 24 hours or more.

Examples of anti-histamines include methapyrilene or loratadine.

Other suitable combinations include, for example, other anti-inflammatory agents eg. NSAIDs (eg. sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (eg. antibiotics, antivirals). Compounds of formula (I) may also be combined with anti-cholinergic compounds, examples of which include ipratropium (eg as bromide), tiotropium, atropine or oxitropium. Any of the aforementioned substances may be employed in the form of alternative salts or solvates thereof.

Of particular interest is use of the compounds of formula (I) in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

Initial experiments were conducted to establish and validate a [$^3$H]-rolipram binding assay. Details of this work are given in the Binding Assays described in detail below.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl [4-(3-cyclopentyloxy-4-methoxyphenyl)pyrrolidine-2-ylidene]acetate; and
(S)-(-)-ethyl [4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 03 Sept. 1996; this patent and the compounds it discloses are incorporated herein in full by reference. The compound of particular interest, which is disclosed in U.S. Pat. No. 5,552,438, is cis-4-cyano-4-[3-(cyclopentyloxy)$_4$-methoxyphenyl]cyclohexane-1-carboxylic acid (also known as cilomalast) and its salts, esters, pro-drugs or physical forms; AWD-12-281 from Astra (Hofgen, N. et al. 15th EFMC Int Symp Med Chem (Sep. 6-10, Edinburgh) 1998, Abst P.98); a 9-benzyladenine derivative nominated NCS-613 (INSERM); D4418 from Chiroscience and Schering-Plough; a benzodiazepine PDE4 inhibitor identified as Cl-1018 (PD-168787; Parke-Davis/Wamer-Lambert); a benzodioxole derivative Kyowa Hakko disclosed in WO 9916766; V-11294A from Napp (Landells, L. J. et al. Eur Resp J [Annu Cong Eur Resp Soc (Sep. 19-23, Geneva) 1998] 1998, 12(Suppl. 28): Abst P2393); roflumilast (CAS reference No 162401-32-3) and a pthalazinone (WO 9947505) from Byk-Gulden; or a compound identified as T-440 (Tanabe Seiyaku; Fuji, K. et al. J Pharmacol Exp Ther, 1998, 284(1): 162).

Phosphodiesterase and Rolipram Binding Assays

Assay method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp1798-1804,1992).

Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM MgCl$_2$, 50 μM 5'-AMP and 1 nM of [$^3$H]-rolipram (Torphy et al., J. of Biol. Chem., Vol. 267, No. 3 pp 1798-1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1 B

Measurement of Phosphodiesterase Activity

PDE activity was assayed using a [$^3$H]cAMP SPA or [$^3$H] cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM MgCl$_2$, 1.7 mM EGTA, [$^3$H]cAMP or [$^3$H] cGMP (approximately 2000 dpm/pmol), enzyme and various concentrations of the inhibitors. The assay was allowed to proceed for 1 hr and was terminated by adding 50 µl of SPA yttrium silicate beads in the presence of zinc sulfate. The plates were shaken and allowed to stand at room temperature for 20 min. Radiolabeled product formation was assessed by scintillation spectrometry.

[$^3$H]R-rolipram Binding Assay

The [$^3$H]R-rolipram binding assay was performed by modification of the method of Schneider and co-workers, see Nicholson, et al., Trends Pharmacol. Sci., Vol. 12, pp. 19-27 (1991) and McHale et al., Mol. Pharmacol., Vol. 39, 109-113 (1991). R-Rolipram binds to the catalytic site of PDE4 see Torphy et al., Mol. Pharmacol., Vol. 39, pp. 376-384 (1991). Consequently, competition for [$^3$H]R-rolipram binding provides an independent confirmation of the PDE4 inhibitor potencies of unlabeled competitors. The assay was performed at 30° C. for 1 hr in 0.5 µl buffer containing (final concentrations): 50 mM Tris-HCl, pH 7.5, 5 mM MgCl$_2$, 0.05% bovine serum albumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

The invention thus provides, in a further aspect, a combination comprising a compound of formula (I) or a physiologically acceptable salt or solvate thereof together with a PDE4 inhibitor.

The combination referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations.

Appropriate doses of known therapeutic agents will be readily appreciated by those skilled in the art.

The compounds of formula (I) and salts and solvates thereof may be prepared by the methodology described hereinafter, constituting a further aspect of this invention.

Thus, according to a first process (A), a compound of formula (I) may be prepared by treating a compound of formula (II)

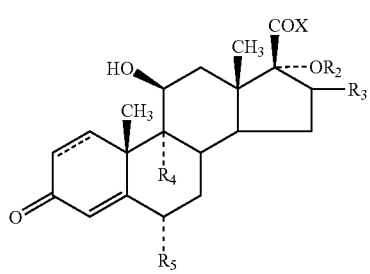

in which $R_2$, $R_3$, $R_4$, $R_5$ and ---- are as defined hereinbefore for compounds of formula (I) and X represents OH, SH or an activated derivative thereof such as a triazole or a mixed anhydride, with a compound of formula (III)

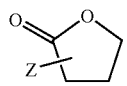

and salts thereof, in which
Z represents OH, NH$_2$ or SH.

Compounds of formula (I) wherein $R_1$ represents O or S may also be prepared according to a second process (B) in which a compound of formula (II) in which $R_2$, $R_3$, $R_4$, $R_5$ and ---- are as defined hereinbefore and X represents OH or SH or their corresponding salts, is treated with a compound of formula (IV) or formula (V)

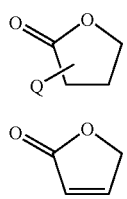

in which Q represents a suitable leaving group (such as Cl, Br, OSO$_2$A wherein A is, for example CH$_3$, CF$_3$, p-CH$_3$C$_6$H$_4$), under standard methods.

The above general process (B) employing compounds of formula (IV) can be used to prepare compounds of formula (I) in which $R_1$ is linked to the alpha, beta, or gamma carbon atoms of the lactone group.

Compounds of formula (I) wherein $R_1$ represents O or S may be prepared according to the above process (B) by alkylation of a compound of formula (II) wherein X represents OH or SH respectively, with a compound of formula (IV) wherein Q represents a suitable leaving group using methods known in the art, or an adaptation of those methods.

Thus, for example, a compound of formula (i) wherein $R_1$ represents O may be prepared by alkylation of a compound of formula (II) wherein X represents OH conveniently in the form of an appropriate salt (such as alkali metal e.g. sodium or quarternaryammonium salt) with a compound of formula (IV) wherein Q represents a suitable leaving group, preferably chlorine, bromine or mesylate. The alkylation reaction is preferably carried out in the presence of a solvent, suitably a polar solvent, under inert conditions, for example, nitrogen or the like, conveniently at a temperature of between about 0° C. to 100° C. Suitable polar solvents may include acetone, dimethylformamide, dimethyl acetamide, dimethylsulphoxide, dichloromethane or chloroform.

Similarly, compounds of formula (I) wherein $R_1$ represents S can be prepared according to the above process (B) by alkylation of a compound of formula (II) wherein X represents SH with a compound of formula (IV) wherein Q represents a suitable leaving group by adaptation of the methods described by Phillipps et al, Journal of Medicinal Chemistry, 1994, 37, 3717-3729. Thus, a compound of formula (I) wherein $R_1$ represents S may be prepared by alkylation of the corresponding compound of formula (II) wherein X represents SH conveniently in the form of an appropriate salt (such as alkali metal e.g. sodium or quarternaryammonium salt) with a compound of formula (IV) wherein Z represents a suitable leaving group as described hereinabove for similar alkylation reactions.

Alternatively, compounds of formula (I) wherein $R_1$ represents O or S may be prepared according to the above process (B) by alkylation of a compound of formula (II) wherein X represents OH or SH with a compound of formula (IV) wherein Q represents OH under Mitsunobu conditions using triphenylphosphine and a dialkyl azodicarboxylate, or by using Vilsmeier methodology as described by Barrett and Procopiou in the Journal of the Chemical Society, Chemical Communications, 1995, 1403-1404.

A compound of formula (I) wherein $R_1$ represents S and is bonded to the beta carbon atom of the lactone group may also be prepared by reacting the corresponding compound of formula (II) wherein X represents SH with a compound of formula (V). For example, by Michael addition of the compound of formula (II) with the compound of formula (V) in the presence of a base such as potassium carbonate and in a suitable solvent such as dimethylformamide.

Compounds of formula (I) may also be prepared from other compounds of formula (I) thereof using conventional interconversion procedures such as epimerisation or esterification. Thus, a process for preparing a compound of formula (I) by interconversion of another compound of formula (I) (process C) constitutes a further aspect of the present invention.

Compounds of formula (I) having a 1,2 single bond may be prepared by partial reduction of the corresponding 1,2 double bond compound by conventional methods. Thus, for example, by hydrogenation of the corresponding compound of formula (I) or of an intermediate used for the preparation of a compound of formula (I) using a palladium catalyst, conveniently in a suitable solvent e.g. ethyl acetate or preferably by using tris(triphenylphosphine) rhodium (I) chloride (known as Wilkinson's catalyst), conveniently in a suitable solvent such as toluene, ethyl acetate or ethanol.

It will be appreciated by those skilled in the art that it may be desirable to use protected derivatives of intermediates used in the preparation of compounds of formula (I). Thus, the above processes may require deprotection as an intermediate or final step to yield the desired compound. Thus, according to another process (D), a compound of formula (I) may be prepared by subjecting a protected derivative of a compound of formula (I) to reaction to remove the protecting group or groups present, constituting a further aspect of the present invention.

Protection and deprotection of functional groups may be effected using conventional means. Thus, hydroxyl groups may be protected using any conventional hydroxyl protecting group, for example, as described in Protective Groups in Organic Chemistry, Ed. J. F. W. McOmie (Plenum Press, 1973) or Protective Groups in Organic Synthesis by Theodora W. Green (John Wiley and Sons, 1991).

Examples of suitable hydroxyl protecting groups includes groups selected from alkyl (e.g. t-butyl or methoxymethyl), aralkyl (e.g. benzyl, diphenylmethyl or triphenylmethyl), heterocyclic groups such as tetrahydropyranyl, acyl (e.g. acetyl or benzoyl) and silyl groups such as trialkylsilyl (e.g. t-butyidimethylsilyl). The hydroxyl protecting groups may be removed by conventional techniques. Thus, for example alkyl, silyl, acyl and heterocyclic groups may be removed by solvolysis, e.g. by hydrolysis under-acidic or basic conditions. Aralkyl groups such as triphenylmethyl may be similarly be removed by solvolysis, e.g. by hydrolysis under acidic conditions. Aralkyl groups such as benzyl may be cleaved by hydrogenolysis in the presence of a Noble metal catalyst such as palladium-on-charcoal.

Compounds of formulae (III), (IV) and (V) are either generally known compounds or may be prepared by methods analogous to those described in the art for preparing the known compounds of formula (III), (IV) and (V) or may be prepared by the methods described herein.

Compounds of formula (II) wherein X represents SH may be prepared from the corresponding 17α-hydroxyl derivative of formula (VI):

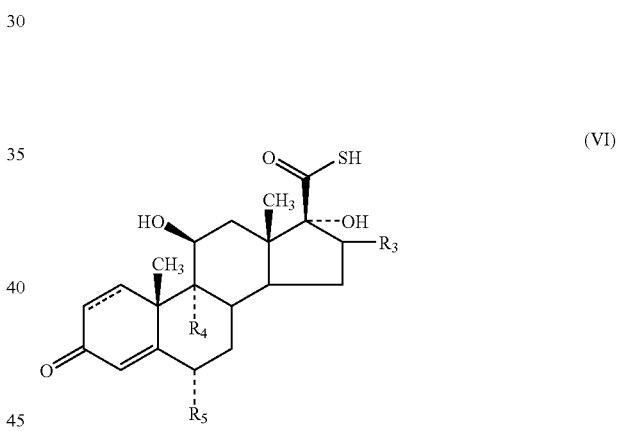

wherein $R^2$, $R^3$, $R^4$, $R^5$ and ≡≡≡are as defined above, using for example, the methodology described by G. H. Phillipps et al., (1994) Journal of Medicinal Chemistry, 37, 3717-3729. For example the step typically comprises the addition of a reagent suitable for performing the esterification to the ester such as an aryl or heteroarylcarbonyl halide eg. 2-furanoyl chloride in the presence of a mild base eg. triethylamine. Generally the aryl or heteroarylcarbonyl halide would be employed in at least 2 times molar quantity relative to the compound of formula (VI). The second mole of aryl or heteroarylcarbonyl halide tends to react with the thioacid moiety in the compound of formula (VI) and would need to be removed by reaction with an amine such as diethylamine.

Compounds of formula (VI) may be prepared in accordance with procedures described in GB 2088877B.

Compounds of formula (VI) may also be prepared by a process comprising the following steps:

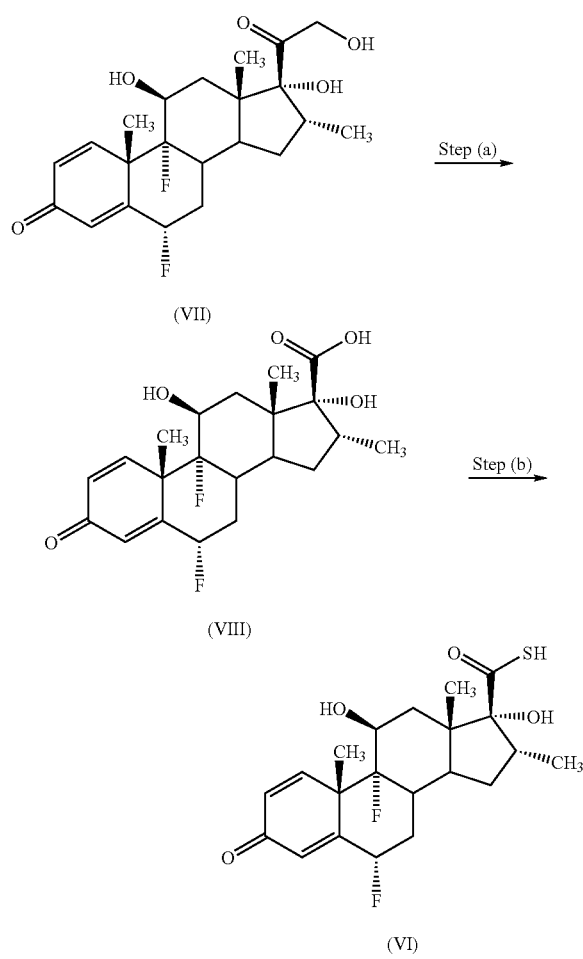

Step (a) comprises oxidation of a solution containing the compound of formula (VII).

Preferably, step (a) will be performed in the presence of a solvent comprising methanol, water, tetrahydrofuran, dioxan or diethylene glygol dimethylether. For example, so as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1-9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg. one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (VIII) may be isolated by recrystallisation from the reaction mixture by addition of an anti-solvent. A suitable anti-solvent for compound of formula (VIII) is water. Surprisingly we have discovered that it is highly desirable to control the conditions under which the compound of formula (VIII) is precipitated by addition of anti-solvent eg water. When the recrystallisation is performed using chilled water (eg water/ice mixture at a temperature of 0-5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no of solvated solvent within the crystal lattice.

Step (b) will typically comprise the addition of a reagent suitable for converting a carboxylic acid to a carbothioic acid eg. using hydrogen sulphide gas together with a suitable coupling agent eg. carbonyldiimidazole (CDI) in the presence of a suitable solvent eg. dimethylformamide.

Solvates of compounds of formula (I) which are not physiologically acceptable may be useful as intermediates in the preparation of compounds of formula (I) or physiologically acceptable solvates thereof.

The advantages of compounds of formula (I) and/or salts and solvates thereof may include the fact that the substances appear to demonstrate excellent anti-inflammatory properties, with predictable pharmacokinetic and pharmacodynamic behaviour, with an attractive side-effect profile (demonstrated, for example, by low thymus weight reduction in rats), long duration of action and are compatible with a convenient regime of treatment in human patients. Further advantages may include the fact that the substances have desirable physical and chemical properties which allow for ready manufacture and storage.

DETAILED DESCRIPTION

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), dt (doublet of triplets) and b (broad). Biotage refers to prepacked silica gel cartridges containing KP-Sil run on flash 12i chromatography module. LCMS was conducted on a Supelcosil LCABZ+PLUS column (3.3 cm×4.6 mm ID) eluting with 0.1% HCO$_2$H and 0.01M ammonium acetate in water (solvent A), and 0.05% HCO$_2$H 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).

Intermediates

Intermediate 1

6α,9α-Difluoro-17α-[(2-furanylcarbonyl)oxy]-11β-hydroxy-16α-methyl-3-oxo-androsta-1,4-diene-17β-carbothioic acid A solution of 6α, 9α-difluoro-11β, 17α-dihydroxy-16α-methyl-3-oxo-androsta-1,4-diene-17β-carbothioic acid (prepared in accordance with the procedure described in GB 2088877B) (189, 43.64 mmol) in anhydrous dichloromethane (200 ml) and triethylamine (15.94 ml, 114 mmol) was treated at <5° C. with a solution of 2-furoyl chloride (11.24 ml, 114 mmol) in anhydrous dichloromethane (100 ml) over approximately 40 min. The solution was stirred at <5° C. for 30 min. The resulting solid was collected by filtration, washed successively with 3.5% aqueous sodium hydrogen carbonate solution, water, 1M hydrochloric acid, and water and dried in vacuo at 60° C. to give a cream coloured solid. The dichloromethane filtrate was washed successively with 3.5% sodium hydrogen carbonate solution, water, 1M hydrochloric acid, water, dried ($Na_2SO_4$) and evaporated to give a cream coloured solid which was combined with that isolated above. The combined solids (26.9 g) were suspended in acetone (450 ml) and stirred. Diethylamine (16.8 ml, 162 mmol) was added and the mixture stirred at room temperature for 4.5 h. The mixture was concentrated and the precipitate collected by filtration and washed with a little acetone. The washings and filtrate were combined, concentrated and loaded onto a silica gel Biotage column which was eluted with 24:1 chloroform:methanol. Fractions which contained the more polar component were combined and evaporated to give a cream coloured solid. This was combined with the solid isolated above and dried in vacuo to give a pale beige coloured solid (19.7 g). This was dissolved in warm water, the pH adjusted to 2 with concentrated hydrochloric acid and the mixture extracted with ethyl acetate. The organic extract was dried ($Na_2SO_4$) and evaporated to give, after drying at 50° C., the title compound as a cream coloured solid (18.081 g, 82%): LCMS retention time 3.88 min, m/z 507 $MH^+$, NMR δ ($CDCl_3$) includes 7.61 (1H, m), 7.18-7.12 (2H, m), 6.52 (1H, dd, J 4, 2 Hz), 6.46 (1H, s), 6.41 (1H, dd, J 10, 2 Hz), 5.47 and 5.35 (1H, 2m), 4.47 (1H, bd, J 9 Hz), 3.37 (1H, m), 1.55 (3H, s), 1.21 (3H, s), 1.06 (3H, d, J 7 Hz).

The following intermediates were prepared using a method analogous to that described for Intermediate 1:

Intermediate 2

6α,9α-Difluoro-17α-[(3-furanylcarbonyl)oxy]-11β-hydroxy-16α-methyl-3-oxo-androsta-1,4-diene-17β-carbothioic acid LCMS retention time 3.75 min, m/z 507 $MH^+$.

Intermediate 3

6α,9α-Difluoro-11β-hydroxy-16α-methyl-3-oxo-17α-[(2-thiophenylcarbonyl)oxy]-androsta-1,4-diene-17β-carbothioic acid LCMS retention time 3.93 min, m/z 523 $MH^+$.

Intermediate 4

6α,9α-Difluoro-11β-hydroxy-16α-methyl-3-oxo-17α-[(3-thiophenylcarbonyl)oxy]-androsta-1,4-diene-17β-carbothioic acid LCMS retention time 3.95 min, m/z 523 $MH^+$.

Intermediate 5

17α-(Benzoyl)oxy-6α,9α-difluoro-11β-hydroxy-16α-methyl-3-oxo-androsta-1,4-diene-17β-carbothioic acid LCMS retention time 4.02 min, m/z 517 $MH^+$.

Intermediate 6

9α-Fluoro-17α-[(2-furanylcarbonyl)oxy]-11β-hydroxy-16β-methyl-3-oxo-androsta-1,4-diene-17β-carbothioic acid Intermediate 6 was prepared from 11β,17α-dihydroxy-9α-fluoro-16β-methyl-3-oxo-androsta-1,4-diene-17β-carbothioic acid (prepared in accordance with the procedure described in Phillips et al, (1994) J. Med. Chem. 37, 3717-3729). LCMS retention time 3.61 min, m/z 489 $MH^+$.

Intermediate 7

6α,9α-Difluoro-11β-hydroxy-16α-methyl-17α-[(5-methylthiophene-2-carbonyl)oxy]-3-oxo-androsta-1,4-diene-17β-carbothioic acid LCMS retention time 4.01 min, m/z 537 $MH^+$ Intermediate 8

6α,9α-Difluoro-11β-hydroxy-17α-[(isoxazole-5-carbonyl)oxy]-16α-methyl-3-oxo-androsta-1,4-diene-17β-carbothioic acid LCMS retention time 3.69 min, m/z 508 $MH^+$ Intermediate 9

17α-[(5-Chlorothiophene-2-carbonyl)oxy]-6α,9α-difluoro-11β-hydroxy-16α-methyl-3-oxo-androsta-1,4-diene-17β-carbothioic acid LCMS retention time 4.36 min, m/z 557/559 $MH^+$ Intermediate 10

6α,9α-Difluoro-17α-[(3,5-dimethylisoxazole-4-carbonyl)oxy]-11β-hydroxy-16α-methyl-3-oxo-androsta-1,4-diene-17β-carbothioic acid LCMS retention time 3.71 min, m/z 536 $MH^+$ Intermediate 11

17α-[(5-Chloro-4-methoxy-thiophene-3-carbonyl)oxy]-6α,9α-difluoro-11β-hydroxy-16α-methyl-3-oxo-androsta-1,4-diene-17β-carbothioic acid LCMS retention time 4.18 min, m/z 587/589 $MH^+$

Intermediate 12

6α,9α-Difluoro-11β-hydroxy-16α-methyl-17α-[(4-methyl-1,2,3-thiadiazole-5-carbonyl)oxy]-3-oxo-androsta-1,4-diene-17β-carbothioic acid LCMS retention time 4.06 min, m/z 539 MH$^+$

Intermediate 13

17α-[(3-Bromothiophene-2-carbonyl)oxy]-6α,9α-difluoro-11β-hydroxy-16α-methyl-3-oxo-androsta-1,4-diene-17β-carbothioic acid LCMS retention time 4.31 min, m/z 6011603 MH$^+$

Intermediate 14

17α-[(2,5-Dichlorothiophene-3-carbonyl)oxy]-6α,9α-difluoro-11β-hydroxy-16α-methyl-3-oxo-androsta-1,4-diene-17β-carbothioic acid LCMS retention time 4.59 min, m/z 591/593/595 MH$^+$

Intermediate 15

17α-[(5-Bromofuran-2-carbonyl)oxy]-6α,9α-difluoro-11β-hydroxy-16α-methyl-3-oxo-androsta-1,4-diene-17β-carbothioic acid LCMS retention time 4.14 min, m/z 585/587 MH$^+$

Intermediate 16

6α,9α-Difluoro-17α-[(2,5-dimethylfuran-3-carbonyl)oxy]-11β-hydroxy-16α-methyl-3-oxo-androsta-1,4-diene-17β-carbothioic acid LCMS retention time 4.02 min, m/z 535 MH$^+$

Intermediate 17

17α-[(3-Chlorothiophene-2-carbonyl)oxy]-6α,9α-difluoro-11β-hydroxy-16α-methyl-3-oxo-androsta-1,4-diene-17β-carbothioic acid LCMS retention time 4.27 min, m/z 557/559 MH$^+$

Intermediate 18

6α,9α-Difluoro-11β-hydroxy-16α-methyl-17α-[(2-methylfuran-3-carbonyl)oxy]-3-oxo-androsta-1,4-diene-17β-carbothioic acid LCMS retention time 3.92 min, m/z 521 MH$^+$

Intermediate 19

6α,9α-Difluoro-11β-hydroxy-16α-methyl-17α-[(3-methylfuran-2-carbonyl)oxy]-3-oxo-androsta-1,4-diene-17β-carbothioic acid LCMS retention time 3.85 min, m/z 521 MH$^+$

Intermediate 20

6α,9α-Difluoro-11β-hydroxy-16α-methyl-17α-[(1-methyl-1H-pyrrole-2-carbonyl)oxy]-3-oxo-androsta-1,4-diene-17β-carbothioic acid LCMS retention time 3.78 min, m/z 520 MH$^+$

Intermediate 21

6α,9α-Difluoro-11β-hydroxy-16α-methyl-3-oxo-17β-[(1,3-thiazole-4-carbonyl)oxy]-androsta-1,4-diene-17β-carbothioic acid LCMS retention time 3.48 min, m/z 524 MH$^+$

Intermediate 22

6α,9α-Difluoro-11β-hydroxy-16α-methyl-17α-[(5-methylisoxazole-3-carbonyl)oxy]-3-oxo-androsta-1,4-diene-17β-carbothioic acid LCMS retention time 3.72 min, m/z 522 MH$^+$

Intermediate 23

6α,9α-Difluoro-17α-[(1,3-dimethyl-1H-pyrazole-5-carbonyl)oxy]-11β-hydroxy-16α-methyl-3-oxo-androsta-1,4-diene-17β-carbothioic acid LCMS retention time 3.72 min, m/z 535 MH$^+$

Intermediate 24

6α,9α-Difluoro-11β-hydroxy-17α-[(isoxazole-3-carbonyl)oxy]-16α-methyl-3-oxo-androsta-1,4-diene-17β-carbothioic acid LCMS retention time 3.78 min, m/z 508 MH$^+$

Intermediate 25

6α,9α-Difluoro-11β-hydroxy-17α-[(4-methoxythiophene-3-carbonyl)oxy]-16α-methyl-3-oxo-androsta-1,4-diene-17β-carbothioic acid LCMS retention time 3.74 min, m/z 553 MH$^+$

Intermediate 26

6α,9α-Difluoro-11β-hydroxy-16α-methyl-3-oxo-17α-[(1,2,3-thiadiazole-4-carbonyl)oxy]-androsta-1,4-diene-17β-carbothioic acid LCMS retention time 3.70 min, m/z 526 MH$^+$

Intermediate 27

6α,9α-Difluoro-11β-hydroxy-16α-methyl-3-oxo-17α-[(1,3-thiazole-5-carbonyl)oxy]-androsta-1,4-diene-17β-carbothioic acid LCMS retention time 4.29 min, m/z 524 MH$^+$

Intermediate 28

6α,9α-Difluoro-11β-hydroxy-17α-[(isothiazole-3-carbonyl)oxy]-16α-methyl-3-oxo-androsta-1,4-diene-17β-carbothioic acid LCMS retention time 4.44 min, m/z 524 MH$^+$

Intermediate 29

6α,9α-Difluoro-11β-hydroxy-17α-[(isothiazole-5-carbonyl)oxy]-16α-methyl-3-oxo-androsta-1,4-diene-17β-carbothioic acid LCMS retention time 4.60 min, m/z 524 MH$^+$

Intermediate 30

6α,9α-Difluoro-11β-hydroxy-16α-methyl-17α-[(3-methylisoxazole-5-carbonyl)oxy]-3-oxo-androsta-1,4-diene-17β-carbothioic acid LCMS retention time 3.84 min, m/z 522 MH$^+$

Examples

Example 1

6α,9α-Difluoro-17α-[(2-furanylcarbonyl)oxy]-11β-hydroxy-16α-methyl-3-oxo-androsta-1,4-diene-17β-carbothioic acid S-(2-oxo-tetrahydro-furan-3S-yl) ester A suspension of Intermediate 1 (500 mg, 0.987 mmol) and methanesulfonic acid 2-oxo-tetrahydro-furan-3R-yl ester (179 mg, 1.0 mmol) in anhydrous N,N-dimethylformamide (5 ml) was treated with anhydrous pyridine (0.162 ml, 2 mmol). The solution was stirred under nitrogen at room temperature for 18 h and was then treated with 2M hydrochloric acid (0.7 ml), heated to 60° C. and treated with a further quantity (2.4 ml) of 2M hydrochloric acid. The mixture was stirred at 50-60° C. for 5 min. and water (12 ml) was then added dropwise. The mixture was allowed to cool to room temperature and the resulting solid was collected by filtration and dried in vacuo at 50° C. The solid was recrystallised from propan-2-ol/water to give, after drying at 50° C., the title compound (433 mg, 74%) as a white crystalline solid: mp. 238-9° C.; LCMS retention time 3.5 min, m/z 591 MH$^+$, NMR δ (CDCl$_3$) includes 7.60 (1H, m), 7.16 (1H, dd, J 10, 2 Hz), 7.12 (1H, d, J 4 Hz), 6.51 (1H dd, J 4, 2 Hz), 6.45 (1H, s), 6.40 (1H, dd, J 10, 2 Hz), 5.47 and 5.35 (1H, 2m), 4.51 (1H, dt, J 9, 4 Hz), 4.43 (1H, m), 4.36 (1H, m), 4.18 (1H, m), 3.39 (1H, m), 1.54 (3H, s), 1.22 (3H, s), 1.08 (3H, d, J 7 Hz).

Example 2

6α, 9β-Difluoro-17α-[(2-furanylcarbonyl)oxy]-11β-hydroxy-16α-methyl-3-oxo-androsta-1,4-diene-17β-carbothioic acid S-(2-oxo-tetrahydro-furan-3-yl)ester Powdered anhydrous sodium hydrogen carbonate (332 mg, 3.95 mmol) was added to a stirred solution of Intermediate 1 (1 g, 1.97 mmol) in dry dimethylformamide (10 ml). The mixture was stirred and α-bromo-γ-butyrolactone (0.365 ml, 3.95 mmol) was added and the mixture stirred at room temperature for 18 h. The mixture was added to 2M hydrochloric acid (300 ml) and the resulting precipitate collected by filtration, washed with water and dried in vacuo at 50° C. The crude product was purified by Biotage chromatography on silica gel using 3:2 cyclohexane:ethyl acetate as eluant, to give the less polar S-isomer of the title compound as a crystalline solid (594 mg, 51%) mp. 238-9° C. which was identical to the material obtained in Example 1 and the more polar R-isomer of the title compound as a crystalline solid (473 mg, 44%): mp. 299° C. (dec); LCMS retention time 3.55 min, m/z 591 MH$^+$, NMR δ (CDCl$_3$+3 drops DMSO-d$_6$) includes 7.64 (1H, m), 7.27 (1H, dd, J 10, 2 Hz), 7.13 (1H, dd, J 4, <2 Hz), 6.54 (1H, dd, J 4, 2 Hz), 6.38-6.31 (2H, m), 5.50 and 5.38 (1H, 2m), 5.08 (1H, m), 4.55 (1H, dt, J 9, 4 Hz), 4.42-4.34 (2H, m), 4.10 (1H, m), 3.38 (1H, m), 1.56 (3H, s), 1.19 (3H, s), 1.04 (3H, d J 7 Hz).

Example 3

6α,9α-Difluoro-17α-[(3-furanylcarbonyl)oxy]-11β-hydroxy-16α-methyl-3-oxo-androsta-1,4-diene-17β-carbothioic acid S-(2-oxo-tetrahydro-furan-3S-yl) ester Example 3 was prepared from Intermediate 2 using a method analogous to that described for Example 1.
LCMS retention time 3.61 min, m/z 591 MH$^+$

Example 4

6α,9α-Difluoro-11β-hydroxy-16α-methyl-3-oxo-17α-[(2-thiophenylcarbonyl)oxy]-androsta-1,4-diene-17β-carbothioic acid S-(2-oxo-tetrahydro-furan-3S-yl)ester Example 4 was prepared from Intermediate 3 using a method analogous to that described for Example 1. LCMS retention time 3.52 min, m/z 607 MH$^+$

Example 5

6α,9α-Difluoro-11β-hydroxy-16α-methyl-3-oxo-17α-[(3-thiophenylcarbonyl)oxy]-androsta-1,4-diene-17β-carbothioic acid S-(2-oxo-tetrahydro-furan-3S-yl)ester Example 5 was prepared from Intermediate 4 using a method analogous to that described for Example 1.
LCMS retention time 3.69 min, m/z 607 MH$^+$

Example 6

17α-(Benzoyl)oxy-6α,9α-difluoro-11β-hydroxy-16α-methyl-3-oxo-androsta-1,4-diene-17β-carbothioic acid S-(2-oxo-tetrahydro-furan-3S-yl)ester Example 6 was prepared from Intermediate 5 using a method analogous to that described for Example 1. LCMS retention time 3.74 min, m/z 601 MH$^+$

Example 7

9α-Fluoro-17α[(2-furanylcarbonyl)oxy]-11β-hydroxy-16β-methyl-3-oxo-androsta-1,4-diene-17β-carbothioic acid S-(2-oxo-tetrahydro-furan-3S-yl) ester Example 7 was prepared from Intermediate 6 using a method analogous to that described for Example 1. LCMS retention time 3.45 min, m/z 573 MH$^+$

Example 8

6α,9α-Difluoro-11β-hydroxy-16α-methyl-17α-[(5-methylthiophene-2-carbonyl)oxy]-3-oxo-androsta-1,4-diene-17β-carbothioic acid S-(2-oxo-tetrahydro-furan-3S-yl)ester Example 8 was prepared from Intermediate 7 using a method analogous to that described for Example 1. LCMS retention time 3.65 min, m/z 621 MH$^+$

Example 9

6α,9α-Difluoro-11β-hydroxy-17α-[(isoxazole-5-carbonyl)oxy]-16α-methyl-3-oxo-androsta-1,4-diene-17β-carbothioic acid S-(2-oxo-tetrahydro-furan-3S-yl)ester Example 9 was prepared from Intermediate 8 using a method analogous to that described for Example 1. LCMS retention time 3.39 min, m/z 592 MH$^+$

Example 10

17α-[(5-Chlorothiophene-2-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl)ester Example 10 was prepared from Intermediate 9 using a method analogous to that described for Example 1. LCMS retention time 3.77 min, m/z 641/643 MH$^+$

Example 11

6α,9α-Difluoro-17α-[(3,5-dimethylisoxazole-4-carbonyl)oxy]-11β-hydroxy-16α-methyl-3-oxo-androsta-1,4-diene-17β-carbothioic acid S-(2-oxo-tetrahydro-furan-3S-yl)ester Example 11 was prepared from Intermediate 10 using a method analogous to that described for Example 1. ICMS retention time 3.52 min, m/z 620 MH$^+$

Example 12

17α-[(5-Chloro-4-methoxy-thiophene-3-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl)ester Example 12 was prepared from Intermediate 11 using a method analogous to that described for Example 1. LCMS retention time 3.89 min, m/z 671/673 MH$^+$

Example 13

6α,9α-Difluoro-11β-hydroxy-16α-methyl-17α-[(4-methyl-1,2,3-thiadiazole-5-carbonyl)oxy]-3-oxo-androsta-1,4-diene-17β-carbothioic acid S-(2-oxo-tetrahydro-furan-3S-yl)ester Example 13 was prepared from Intermediate 12 using a method analogous to that described for Example 1. LCMS retention time 3.54 min, m/z 623 MH$^+$

Example 14

17α-[(3-Bromothiophene-2-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl)ester Example 14 was prepared from Intermediate 13 using a method analogous to that described for Example 1. LCMS retention time 3.83 min, m/z 685/687 MH$^+$

Example 15

17α-[(2,5-Dichlorothiophene-3-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl)ester Example 15 was prepared from Intermediate 14 using a method analogous to that described for Example 1. LCMS retention time 4.08 min, m/z 675/677/679 MH$^+$

Example 16

17α-[(5-Bromofuran-2-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl) ester Example 16 was prepared from Intermediate 15 using a method analogous to that described for Example 1. LCMS retention time 3.77 min, m/z 669/671 MH$^+$

Example 17

6α,9α-Difluoro-17α-[(2,5-dimethylfuran-3-carbonyl)oxy]-11β-hydroxy-16α-methyl-3-oxo-androsta-1,4-diene-17β-carbothioic acid S-(2-oxo-tetrahydro-furan-3S-yl)ester Example 17 was prepared from Intermediate 16 using a method analogous to that described for Example 1. LCMS retention time 3.82 min, m/z 619 MH$^+$

Example 18

17α-[(3-Chlorothiophene-2-carbonyl)oxy]-6α,9α-difluoro-11β-hydroxy-16α-methyl-3-oxo-androsta-1,4-diene-17β-carbothioic acid S-(2-oxo-tetrahydro-furan-3S-yl)ester Example 18 was prepared from Intermediate 17 using a method analogous to that described for Example 1. LCMS retention time 3.80 min, m/z 641/643 MH$^+$

Example 19

6α,9α-Difluoro-11β-hydroxy-16α-methyl-17α-[(2-methylfuran-3-carbonyl)oxy]-3-oxo-androsta-1,4-diene-17β-carbothioic acid S-(2-oxo-tetrahydro-furan-3S-yl)ester Example 19 was prepared from Intermediate 18 using a method analogous to that described for Example 1. LCMS retention time 3.66 min, m/z 605 MH$^+$

Example 20

6α,9α-Difluoro-11β-hydroxy-16α-methyl-17α-[(3-methylfuran-2-carbonyl)oxy]-3-oxo-androsta-1,4-diene-17β-carbothioic acid S-(2-oxo-tetrahydro-furan-3S-yl)ester Example 20 was prepared from Intermediate 19 using a method analogous to that described for Example 1. LCMS retention time 3.60 min, m/z 605 MH$^+$

Example 21

6α,9α-Difluoro-11β-hydroxy-16α-methyl-17α-[(1-methyl-1H-pyrrole-2-carbonyl)oxy]-3-oxo-androsta-1,4-diene-17β-carbothioic acid S-(2-oxo-tetrahydro-furan-3S-yl)ester Example 21 was prepared from Intermediate 20 using a method analogous to that described for Example 1. LCMS retention time 3.53 min, m/z 604 MH$^+$

Example 22

6α,9α-Difluoro-11β-hydroxy-16α-methyl-3-oxo-17α-[(3-thiazole-4-carbonyl)oxy]-androsta-1,4-diene-17β-carbothioic acid S-(2-oxo-tetrahydro-furan-3S-yl) ester Example 22 was prepared from Intermediate 21 using a method analogous to that described for Example 1. LCMS retention time 3.26 min, m/z 608 MH$^+$

Example 23

6α,9α-Difluoro-11β-hydroxy-16α-methyl-17α-[(5-methylisoxazole-3-carbonyl)oxy]-3-oxo-androsta-1,4-diene-17β-carbothioic acid S-(2-oxo-tetrahydro-furan-3S-yl)ester Example 23 was prepared from Intermediate 22 using a method analogous to that described for Example 1. LCMS retention time 3.58 min, m/z 606 MH$^+$

Example 24

6α,9α-Difluoro-17α-[(1,3-dimethyl-1H-pyrazole-5-carbonyl)oxy]-11β-hydroxy-16α-methyl-3-oxo-androsta-1,4-diene-17β-carbothioic acid S-(2-oxo-tetrahydro-furan-3S-yl)ester Example 24 was prepared from Intermediate 23 using a method analogous to that described for Example 1. LCMS retention time 3.40 min, m/z 619 MH$^+$

Example 25

6α,9α-Difluoro-11β-hydroxy-17α[(isoxazole-3-carbonyl)oxy]-16α-methyl-3-oxo-androsta-1,4-diene-17β-carbothioic acid S-(2-oxo-tetrahydro-furan-3S-yl) ester Example 25 was prepared from Intermediate 24 using a method analogous to that described for Example 1. LCMS retention time 3.36 min, m/z 592 MH$^+$

Example 26

6α,9α-Difluoro-11β-hydroxy-17α-[(4-methoxy-thiophene-3-carbonyl)oxy]-16α-methyl-3-oxo-androsta-1,4-diene-17β-carbothioic acid S-(2-oxo-tetrahydro-furan-3S-yl)ester Example 26 was prepared from Intermediate 25 using a method analogous to that described for Example 1. LCMS retention time 3.54 min, m/z 637 MH$^+$

Example 27

6α,9α-Difluoro-11β-hydroxy-16α-methyl-3-oxo-17α-[(1,2,3-thiadiazole-4-carbonyl)oxy]-androsta-1,4-diene-17β-carbothioic acid S-(2-oxo-tetrahydro-furan-3S-yl)ester Example 27 was prepared from Intermediate 26 using a method analogous to that described for Example 1. LCMS retention time 3.34 min, m/z 609 MH$^+$

Example 28

6α,9α-Difluoro-11β-hydroxy-16α-methyl-3-oxo-17α-[(1,3-thiazole-5-carbonyl)oxy]-androsta-1,4-diene-17β-carbothioic acid S-(2-oxo-tetrahydro-furan-3S-yl) ester Example 28 was prepared from Intermediate 27 using a method analogous to that described for Example 1. LCMS retention time 3.30 min, m/z 608 MH$^+$

Example 29

6α,9α-Difluoro-11β-hydroxy-17α-[(isothiazole-3-carbonyl)oxy]-16α-methyl-3-oxo-androsta-1,4-diene-17β-carbothioic acid S-(2-oxo-tetrahydro-furan-3S-yl) ester Example 29 was prepared from Intermediate 28 using a method analogous to that described for Example 1. LCMS retention time 3.38 min, m/z 608 MH$^+$

Example 30

6α,9α-Difluoro-11β-hydroxy-17α-[(isothiazole-5-carbonyl)oxy]-16α-methyl-3-oxo-androsta-1,4-diene-17β-carbothioic acid S-(2-oxo-tetrahydro-furan-3S-yl) ester Example 30 was prepared from Intermediate 29 using a method analogous to that described for Example 1. LCMS retention time 3.46 min, m/z 608 MH$^+$

Example 31

6α,9α-Difluoro-11β-hydroxy-16α-methyl-17α-[(3-methylisoxazole-5-carbonyl)oxy]-3-oxo-androsta-1,4-diene-17β-carbothioic acid S-(2-oxo-tetrahydro-furan-3S-yl)ester Example 31 was prepared from Intermediate 30 using a method analogous to that described for Example 1. LCMS retention time 3.42 min, m/z 606 MH$^+$ Preparation of long acting β$_2$-adrenoreceptor agonist

Example X 3-(4-{[6-({(2R)-2-Hydroxy-2-[4-hydroxy-3-(hydroxymethyl)phenyl]ethyl}amino)-hexyl]oxy}butyl)benzenesulfonamide acetate i) Di(tert-butyl) 2-(2,2-dimethyl-4H-1,3-benzodioxin-6-yl)-2-oxoethylimidodicarbonate Cesium carbonate (70.4 g) was added to a stirred suspension of 2-bromo-1-(2,2-dimethyl-4H-1,3-benzodioxin-6-yl)ethanone, (Glaxo, DE 3513885, 1985) (61.8 g) and di-t-butyl iminodicarboxylate (47.15 g) in acetonitrile (600 ml) under nitrogen. After vigorous stirring at 21° C. for 24 h the mixture was diluted with water (ca800 ml) and the product was extracted with diethyl ether (1 litre, then 200 m!). The combined organic layers were washed with brine, dried ($MgSO_4$) and concentrated to ca400 ml. The white crystals were collected by filtration, washed with diethyl ether and dried to give the title compound (24.4 g) δ ($CDCl_3$) 7.78(1H, dd, J 8, 2 Hz), 7.65 (1H, brs), 6.87(1H, d, J 8 Hz), 4.97(2H, s), 4.88(2H, s), 1.56(6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

ii) tert-Butyl 2-(2,2-dimethyl-4H-1,3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 litres) at 21° C. and the reaction was stirred for 1.5 h. Aqueous NaOH solution (1.75 litres) was added and after 10 min the phases were separated. The organic layer was washed with water, dried ($MgSO_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

iii) tert-Butyl (2R)-2-(2,2-dimethyl-4H-1,3-benzodioxin-6-yl)-2-hydroxyethylcarbamate A 2M solution of borane—dimethyl sulphide in THF (28 ml) was added slowly to a 1M solution of (R)-tetrahydro-1-methyl-3,3-diphenyl-1H,3H-pyrrolo[1,2-c][1,3,2]oxazaborole in toluene (56 ml) at 0° C. under nitrogen. A solution of tert-butyl 2-(2,2-dimethyl-4H-1,3-benzodioxin-6-yl)-2-oxoethylcarbamate, (108.2 g) in THF (1.3 litres) was added slowly keeping the temperature below 5° C. followed by 2M solution of borane—dimethyl sulphide in THF (252 ml) over 50 min. After 1 h, 2M HCl (170 ml) was added with cooling and the mixture was partitioned between ethyl acetate and water. The organic layer was washed with saturated $NaHCO_3$ solution and brine and dried ($MgSO_4$). The solution was concentrated and the product purified by chromatography on flash silica gel (800 g), eluting successively with hexane:ethyl acetate (4:1 then 3:1) to give the title compound (93.3 g), LCMS RT=3.31 min.

iv) (5R)-5-(2,2-Dimethyl-4H-1,3-benzodioxin-6-yl)-1,3-oxazolidin-2-one tert-Butyl (2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° C. under nitrogen. The mixture was stirred at 21° C. for 2 h. The mixture was recooled to 0° C. and 2M HCl (134 ml) was added. The mixture was diluted with water and the product was extracted with ethyl acetate twice. The solution was washed with brine twice, dried ($MgSO_4$) and evaporated to give the title compound (63.55 g) LCMS RT=2.66 min.

v) 6-Bromohexyl but-3-ynyl ether

3-Butyn-1-ol (42.4 ml) was stirred vigorously with 1,6-dibromohexane (260 ml) and tetrabutylammonium bisulphate (2.4 g) in 50% aqueous sodium hydroxide solution (200 ml) under nitrogen for 3 days. Water (ca 700 ml) was added and the organic layer was separated. The aqueous layer was extracted twice with dichloromethane (2×100 ml) and the combined organic layers were washed with water, dried ($MgSO_4$) and concentrated. The residue in petroleum ether (bp 40-60°) was loaded onto a column of silica gel (1.5 kg) and the column was eluted with petroleum ether (bp 40-60° C.), then 10% diethyl ether in petroleum ether (bp 40-60° C.) to give the title compound (103.3 g), δ ($CDCl_3$) 3.56(2H, t, J 7 Hz), 3.47(2H, t, J 7 Hz), 3.42(2H, t, J 7 Hz), 2.45(2H, m), 1.99(1H, t, J 2 Hz), 1.87(2H, m), 1.60(2H, m) and 1.50 to 1.33 (4H, m).

vi) (5R)-3-[6-(But-3-ynyloxy)hexyl]-5-(2,2-dimethyl-4H-1,3-benzodioxin-6-yl)-1,3-oxazolidin-2-one (5R)-5-(2,2-dimethyl-4H-1,3-benzodioxin-6-yl)-1,3-oxazolidin-2-one (10 g) in DMF (100 ml) was added dropwise to a stirred suspension of sodium hydride (60% oil dispersion, 2.33 g) in DMF (50 ml) with stirring under nitrogen and maintaining the internal temperature at 0° C. Stirring was continued at 0-5° C. for 1 h. The mixture was recooled to 0° C. and a solution of 6-bromohexyl but-3-ynyl ether (14.7 g) in DMF (50 ml) was added over 1 min. The mixture was then stirred at 20-30° C. for 2 h. 2M HCl (9 ml) was added and the mixture was partitioned between water and diethyl ether. The aqueous layer was extracted with more diethyl ether and the combined organic layers were washed twice with brine. After drying ($MgSO_4$) the solution was concentrated and loaded onto a column of silica gel (600 g) set up in diethyl ether:petroleum ether (bp 40-60° C.) (1:2). The column was eluted successively with this mixture, then (1:1) and then diethyl ether to give the title compound (13.88 g) LCMS RT=3.45 min.

vii) 3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide (5R)-3-[6-(But-3-ynyloxy)hexyl]-5-(2,2-dimethyl-4H-1, 3-benzodioxin-6-yl)-1,3-oxazolidin-2-one (1.79 g) was stirred with 3-iodobenzene sulphonamide (1.4 g) in acetonitrile:triethylamine (1:1, 42 ml) under nitrogen for 10 min. Cuprous iodide (0.083 g) and dichlorobis(triphenylphosphine)palladium (0.192 g) were added and the mixture was stirred for 17 h under nitrogen at 21° C. The mixture was evaporated to dryness and the residue was chromatographed on silica gel (250 g) in 30% ethyl acetate: petroleum ether (bp 40-60°), then 50%, then 75% and finally ethyl acetate to give the title compound (2.35 g), LCMS RT=3.44 min.

viii) 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide 3-[4-({6-[(5R)-5-(2,2-Dimethyl-4H-1,3-benzodioxin-6-yl)-2-oxo-1,3-oxazolidin-3-yl]hexyl}oxy)but-1-ynyl]benzenesulfonamide (2.35 g) was stirred with platinum oxide (0.3 g) in THF (30 ml) under hydrogen for 2 h. The catalyst was removed by filtration using a filter aid and the filter cake was leached with ethyl acetate. The combined filtrates were passed through silica gel (200 g) in ethyl acetate and the eluate was evaporated to give the title compound (2.32 g), LCMS RT=3.49 min.

ix) 3-{4-[(6-{[(2R)-2-(2,2-Dimethyl-4H-1,3-benzodioxin-6-yl)-2-hydroxyethyl]amino}hexyl)oxy]butyl}benzenesulfonamide 3-[4-({6-[(5R)-5-(2,2-Dimethyl-4H-1,3-benzodioxin-6-yl)-2-oxo-1,3-oxazolidin-3-yl]hexyl}oxy)butyl]benzenesulfonamide (0.43 g) was stirred in THF (10 ml) while purging with a vigorous stream of nitrogen for 5 min. Potassium trimethylsilanoate (0.43 g) was added and the mixture was stirred at 70° C. under nitrogen for 2.5 h. The mixture was partitioned between dichloromethane and pH 6.4 phosphate buffer and the aqueous layer was extracted with more dichloromethane. The combined organic layers were washed with water, dried ($MgSO_4$) and concentrated. The residue was purified on silica gel (60 g), eluting successively with ethyl acetate:petroleum ether (bp 40-60° C.) (1:1), ethyl acetate, 10% then 20% methanol in ethyl acetate to give the title compound (0.286 g), LCMS RT=2.56 min.

x) 3-(4-{[6-({(2R)-2-Hydroxy-2-[4-hydroxy-3-(hydroxymethyl)phenyl]ethyl}amino)-hexyl]oxy}butyl)benzenesulfonamide acetate 3-{4-[(6-{[(2R)-2-(2,2-dimethyl-4H-1,3-benzodioxin-6-yl)-2-hydroxyethyl]amino}hexyl)oxy]butyl}benzenesulfonamide (0.283 g) was stirred with acetic acid (8 ml) and water (4 ml) at 700 for 35 min before evaporating to dryness. The residue was re-evaporated twice with toluene to give the title compound (0.318 g) LCMS RT=2.34 min, ES+ve 495 $(MH)^+$.

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

The functional assay was based on that described by K. P. Ray et al., Biochem J. (1997), 328, 707-715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which $EC_{50}$ values were estimated.

In this test the compounds of Examples 1 to 10, 13, 14 and 16-31 showed an $EC_{50}$ value of <20 nM. In this test the compounds of Examples 11, 12 and 15 showed EC50 values of 28, 40 and 16 nM respectively. The compound of Example 1 was significantly more potent ($EC_{50}$ 0.95 nM) in this assay than the previously described 17α-propionate ester analogue (Example 2, WO 97/24365) ($EC_{50}$ 2.7 nM).

In Vivo Pharmacological Activity

Pharmacological activity in vivo was assessed using an oxazolone induced contact hypersensitivity model in Balb/c mice similar to that described by Cumberbatch et al., Immunology (2002), 105, 466-477.

Balb/c female mice (18-20 g) were sensitised to oxazolone by the addition of 50 μl to the shaved right flank, of 2.5% oxazolone in acetone:olive oil (4:1). Control (unsensitised) mice were dosed with acetone:olive oil. Five days later all mice were challenged by the addition of 25 μl of 0.25% oxazolone in acetone olive oil (4:1) to the dorsal surface of both ears under isoflourane anaesthesia. 10 μl of solution of test compound at the appropriate concentration or vehicle (absolute ethanol) was applied to the dorsal surface of the right ear 1 hour prior to and 3 hours post oxazolone challenge under isoflourane anaesthesia. The left ear remained untreated to allow assessment of systemic exposure. Ear thickness measurements were taken using an engineer's micrometer prior to the addition of steroid and again 24 hours post oxazolone challenge. Results expressed as the percentage inhibition of ear swelling, from which $EC_{50}$ values were calculated.

In this model the compound of Example 1 showed similar potency ($EC_{50}$ 0.3 μg) to betamethasone valerate and was significantly more potent than the corresponding 17α-propionate ester (Example 2, WO 97/24365) ($EC_{50}$ 1 μg).

Systemic steroid effects were assessed in a rat model of thymus involution. Male CD rats were dosed intra-tracheally daily for 3 days with saline vehicle (20 μl Tween 80 in 100 ml saline) or with a suspension of test compound (dose volume 200 μL). On day 4 the animals were culled and the thymus removed and weighed.

In this model the compound of Example 1 showed no effect on thymus weight when dosed at 1000 μg/day whereas in the same study a 100 mg/day dose of budesonide resulted in a 65% reduction in thymus weight.

Hydrolysis in Human Plasma

Compounds were incubated at 37° in human plasma at a concentration of 5 μg/ml. Aliquots were taken at time 0 and every 30 seconds for the next 10 minutes and were extracted by protein precipitation and analysed by LC-MS/MS. The compound of Example 1 was rapidly hydrolysed showing a half-life of 1.2 min.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

The invention claimed is:

1. A compound of formula (I)

(I)

wherein
$R_1$ represents O, S or NH;
$R_2$ represents —C(=O)-aryl or —C(=O)-heteroaryl;
$R_3$ represents hydrogen, methyl (which may be in either the α or β configuration) or methylene;
$R_4$ and $R_5$ are the same or different and each represents hydrogen or halogen; and
====represents a single or a double bond;
and salts and solvates thereof.

2. A compound according to claim 1 in which $R_1$ represents O or S.

3. A compound according to claim 2 in which $R_1$ represents S.

4. A compound according to claim 1 in which $R_1$ is bonded to the alpha carbon atom of the lactone moiety.

5. A compound according to claim 1, in which $R_2$ represents —C(=O)-heteroaryl.

6. A compound according to claim 5 in which heteroaryl represents a 5 membered heterocyclic aromatic ring containing 3 heteroatoms selected from O, N and S which may optionally be substituted.

7. A compound according to claim 5 in which $R_2$ represents —C(=O)-furanyl, —C(=O)-thiophenyl or —C(=O)-thiophenyl.

8. A compound according to claim 7 in which $R_2$ represents —C(=O)-furanyl.

9. A compound according to claim 8 in which $R_2$ represents —C(=O)-2-furanyl.

10. A compound according to claim 1 in which $R_3$ is methyl.

11. A compound according claim 1 in which $R_4$ and $R_5$ are the same or different and each represents hydrogen, fluorine or chlorine.

12. A compound according to claim 1 in which $R_4$ and $R_5$ are the same or different and each represents hydrogen or fluorine.

13. A compound according to claim 1 which both $R_4$ and $R_5$ are fluorine.

14. A compound according to claim 1 in which $R_1$ is S; $R_2$ is —C(=O)-2-furanyl; $R_3$ is methyl; $R_4$ and $R_5$ are the same or different and each represents hydrogen or fluorine; and ----represents a single or a double bond.

15. A compound according to claim 14 in which $R_4$ and $R_5$ are each fluorine.

16. A compound according to claim 1 in which ----represents a double bond.

17. A compound of formula (I) according to claim 1 which is 6α, 9α-difluoro-17α-[(2-furanylcarbonyl)oxy]-11β-hydroxy-16α-methyl-3-oxo-androsta-1,4-diene-17β-carbothioic acid S— (2-oxo-tetrahydro-furan-3-yl)ester or a solvate thereof.

18. A compound of formula (I) according to claim 1 which is 6α, 9α-difluoro-17α-[(2-furanylcarbonyl)oxy]-11β-hydroxy-16α-methyl-3-oxo-androsta-1,4-diene-17β-carbothioic acid S-(2-oxo-tetrahydro-furan-3S-yl)ester or a solvate thereof.

19. A pharmaceutical composition comprising a compound of formula (I) as defined in claim 1 or a physiologically acceptable salt or solvate thereof in admixture with one or more physiologically acceptable diluents or carriers.

20. A pharmaceutical aerosol formulation comprising a compound of formula (I) as defined in claim 1 or a physiologically acceptable salt or solvate thereof, and a fluorocarbon or hydrogen-containing chlorofluoro carbon as propellant, optionally in combination with a surfactant and or a cosolvent.

21. A pharmaceutical composition according to claim 19 which further comprises another therapeutically active agent.

22. A pharmaceutical composition according to claim 21 in which said another therapeutically active agent is a long acting $β_2$-adrenoreceptor agonist.

23. A pharmaceutical composition according to claim 22 in which said $β_2$-adrenoreceptor agonist is a compound of formula (X):

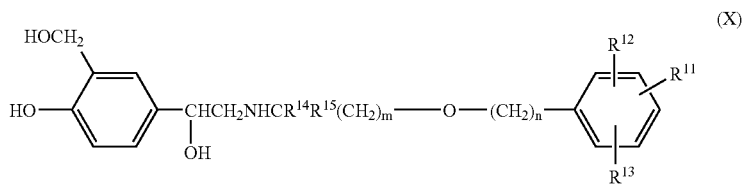

or a salt or solvate thereof, wherein:
m is an integer of from 2 to 8;
n is an integer of from 3 to 11,
with the proviso that m+n is 5 to 19,
$R^{11}$ is —$XSO_2NR^{16}R^{17}$ wherein X is —$(CH_2)_p$— or $C_{2-6}$ alkenylene;
$R^{16}$ and $R^{17}$ are independently selected from hydrogen, $C_{1-6}$alkyl, $C_{3-7}$cycloalkyl, $C(O)NR^{18}R^{19}$, phenyl, and phenyl ($C_{1-4}$alkyl)-,
or $R^{16}$ and $R^{17}$, together with the nitrogen to which they are bonded, form a 5-, 6-, or 7-membered nitrogen containing ring, and $R^{16}$ and $R^{17}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, —$CO_2R^{18}$, —$SO_2NR^{18}R^{19}$, —$CONR^{18}R^{19}$, —$NR^{18}C(O)R^{19}$, or a 5-, 6- or 7-membered heterocylic ring;
$R^{18}$ and $R^{19}$ are independently selected from hydrogen, $C_{1-6}$alkyl, $C_{3-6}$cycloalkyl, phenyl, and phenyl ($C_{1-4}$alkyl)—; and
p is an integer of from 0 to 6;
$R^{12}$ and $R^{13}$ are independently selected from hydrogen, $C_{1-6}$alkyl, $C_{1-6}$alkoxy, halo, phenyl, and $C_{1-6}$haloalkyl; and
$R^{14}$ and $R^{15}$ are independently selected from hydrogen and $C_{1-4}$alkyl with the proviso that the total number of carbon atoms in $R^{14}$ and $R^{15}$ is not more than 4.

24. A pharmaceutical composition according to claim 23 in which the compound of formula (X) is 3-(4-{[6-({(2R)-2-Hydroxy-2-[4-hydroxy-3-(hydroxymethyl)phenyl] ethyl}amino)-hexyl]oxy}butyl)benzenesulfonamide or a salt or solvate thereof.

25. A pharmaceutical composition according to claim 22 suitable for once-per-day administration.

26. A method for the treatment of a human or animal subject with an inflammatory and/or allergic condition, which method comprises administering to said human or animal subject an effective amount of a compound of formula (I) as defined in claim 1 or a physiologically acceptable salt or solvate thereof.

* * * * *